US011452976B2

(12) United States Patent
Ramakrishna et al.

(10) Patent No.: US 11,452,976 B2
(45) Date of Patent: Sep. 27, 2022

(54) MIXING SYSTEM

(71) Applicant: Global Life Sciences Solutions USA LLC, Marlborough, MA (US)

(72) Inventors: Manoj Ramakrishna, Karnataka (IN); Sebastian John, Karnataka (IN); Anoop Bhargav, Karnataka (IN); Haresh Digambar Patil, Karnataka (IN); Praveen Paul, Karnataka (IN)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 411 days.

(21) Appl. No.: 16/474,376

(22) PCT Filed: Dec. 22, 2017

(86) PCT No.: PCT/EP2017/084480
§ 371 (c)(1),
(2) Date: Jun. 27, 2019

(87) PCT Pub. No.: WO2018/122192
PCT Pub. Date: Jul. 5, 2018

(65) Prior Publication Data
US 2019/0388855 A1    Dec. 26, 2019

(30) Foreign Application Priority Data
Dec. 29, 2016    (IN) .............................. 201611044896

(51) Int. Cl.
*B22C 5/00*    (2006.01)
*B01F 35/22*    (2022.01)
(Continued)

(52) U.S. Cl.
CPC ........ *B01F 35/2202* (2022.01); *B01F 33/846* (2022.01); *B01F 33/8442* (2022.01);
(Continued)

(58) Field of Classification Search
CPC ................................................ B01F 15/00285
See application file for complete search history.

(56) References Cited

U.S. PATENT DOCUMENTS 4,618,586 A * 10/1986 Walker ................. A01N 1/0247
435/286.5
6,511,842 B1    1/2003 Lamare et al.
(Continued)

FOREIGN PATENT DOCUMENTS

CN    105392877 A    3/2016
DE    202007000140 U1    4/2007
(Continued)

OTHER PUBLICATIONS

PCT International Search Report and Written Opinion for PCT Application No. PCT/EP2017/084480 dated Apr. 9, 2018 (10 pages).
(Continued)

*Primary Examiner* — Anshu Bhatia
*Assistant Examiner* — Gregory Y Huan
(74) *Attorney, Agent, or Firm* — Eversheds Sutherland (US) LLP

(57) ABSTRACT

The present invention relates to a mixing system for a bioreactor, comprising a plurality of supply units (10), each being able to hold media for use in a bioreactor a mixing unit (30) for creating a uniform mixing of media a first feeding mechanism (20), arranged to feed media from the supply units (10) into the mixing unit (30), a control unit (40) operatively connected to the first feeding mechanism (20) and the mixing unit (30), said control unit (40) being configured to control the first feeding mechanism (20) to feed predetermined amounts of media from the plurality of supply units (10) to the mixing unit (30), and further being configured to control the mixing unit (30) to create a uniform
(Continued)

Figure 1:
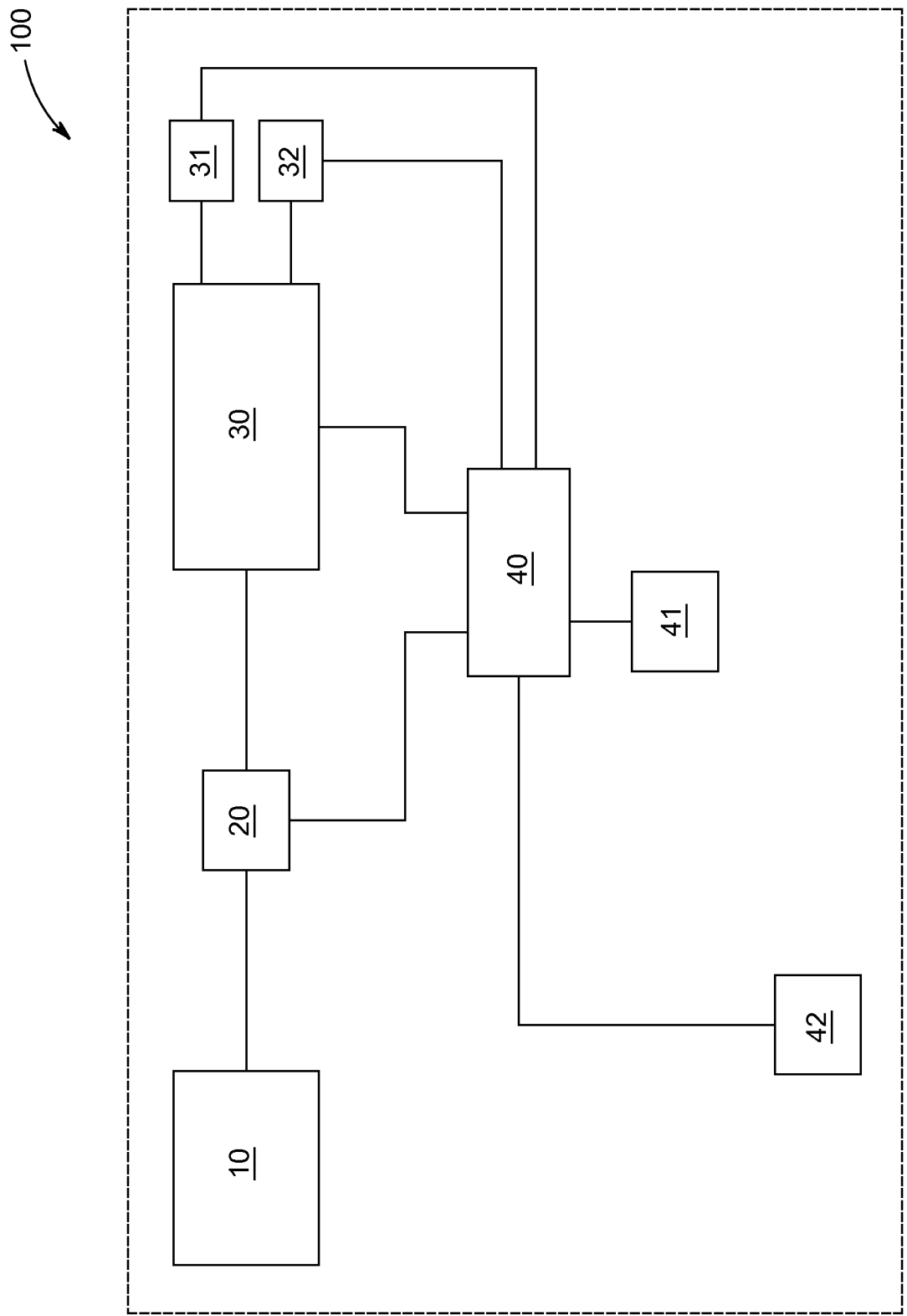

mixing of media. The invention also relates to a method for mixing media for use in a bioreactor.

14 Claims, 8 Drawing Sheets

(51) Int. Cl.
  *C12M 1/02* (2006.01)
  *B01F 33/84* (2022.01)
  *C12M 1/00* (2006.01)
  *B01F 35/90* (2022.01)
  *B01F 35/21* (2022.01)
  *B01F 35/71* (2022.01)
(52) U.S. Cl.
  CPC ......... *C12M 27/00* (2013.01); *B01F 35/2132* (2022.01); *B01F 35/717611* (2022.01); *B01F 35/90* (2022.01); *B01F 2035/99* (2022.01); *C12M 21/00* (2013.01); *C12M 23/40* (2013.01)

(56) References Cited

U.S. PATENT DOCUMENTS

2003/0198125 A1* 10/2003 Linsen ................ B01F 13/1066
                                                                  366/152.1
2004/0250873 A1* 12/2004 Taylor ............... B01F 15/00194
                                                                  141/83
2015/0257974 A1*  9/2015 Demers ............... B01F 13/1066
                                                                  206/438

FOREIGN PATENT DOCUMENTS

| GB | 2515751 A1 | 1/2015 | | |
|----|------------|--------|---|---|
| JP | 04004892 A | 1/1992 | | |
| JP | H044892 A | 1/1992 | | |
| WO | 2006/122089 A2 | 11/2006 | | |
| WO | WO-2006122089 A2 * | 11/2006 | ............ | C12M 23/42 |
| WO | 2010/135377 A1 | 11/2010 | | |
| WO | WO-2010135377 A1 * | 11/2010 | .............. | C12P 19/14 |
| WO | WO-2016124505 A1 * | 8/2016 | .......... | B01F 15/0085 |

OTHER PUBLICATIONS

Japanese Office Action for JP Application No. 2019-535946 dated Apr. 12, 2021 (7 pages with English translation).
CN, "Office Action" App. No. 201780087579.1, dated Mar. 19, 2022, 15 pages.

* cited by examiner

MIXING SYSTEM

CROSS REFERENCE TO RELATED APPLICATIONS

This application claims the priority benefit of PCT/EP2017/084480 filed on Dec. 22, 2017, which claims priority benefit of Indian Application No. 201611044896 filed on Dec. 29, 2016. The entire contents of which are hereby incorporated by reference herein.

TECHNICAL FIELD

The present invention relates to a mixing system for a bioreactor and to a method for mixing media for use in a bioreactor.

BACKGROUND

The use of bioreactors for cultivation of cell samples is well known within the art. Generally, media is introduced into a cell bag and conditions closely monitored to optimize the cultivation process. The media is often created through mixing several media types in order to arrive at a mixture having suitable properties, before said media is fed into the cell bag.

Today, the media is often prepared through a multi-step process that is time consuming and cumbersome. Some improvements have been suggested, for instance through U.S. Pat. Nos. 5,350,080 A, 5,069,370 A, 5,686,304 A, 5,941,635 A, 6,923,567 B2, 6,908,223 B2, and 8,272,255 B2.

There is, however, a further need for improvements in order to achieve an efficient and reliable mixing of media without the drawbacks of the prior art methods and systems.

SUMMARY OF THE INVENTION

The object of the present invention is to eliminate or at least to minimize the problems mentioned above. This is achieved through a mixing system according to the appended independent claim. Thanks to the invention, media for a bioreactor may be mixed and prepared without the need for input or actions from a human operator or user, and the media preparation process is significantly improved and the risk of contamination to the media decreased. The mixing system of the invention may act independently or controlled by external units or operators, as desired, and may also use feedback within the system for checking the quality of prepared media and further improve the media mixture in response to such feedback.

According to one aspect of the invention, the mixing system is integrated with a bioreactor. Thereby, the operation of the bioreactor and the preparation of media may be performed together, allowing for fewer controls and components and creating an independent system for cell cultivation where media having suitable properties is automatically prepared and supplied as needed.

According to another aspect of the invention, the first feeding mechanism comprises peristaltic pumps for pumping media from each supply unit to the mixing unit. Preferably, the peristaltic pumps are controlled by at least one stepper motor. Thereby, the first feeding mechanism can be controlled in a simple yet efficient way and provide the desired media portions as determined by the control unit.

According to another aspect of the invention, the first feeding mechanism comprises valves for controlling a flow of media from each supply unit to the mixing unit. Thereby, the feeding of media portions to the mixing unit can be performed in a simple and efficient way, requiring fewer components and thereby rendering the mixing system more cost efficient.

According to another aspect of the invention, the bioreactor is operatively connected to and able to control the operation of the control unit. Thereby, the mixing system can serve as a slave to the bioreactor and perform its operation in accordance with the direct instructions of the bioreactor, but with a separate control unit from that of the bioreactor to enable processes to be carried out in parallel without demanding a more advanced control unit. This also allows the mixing system to be a separate system that is connected to any suitable bioreactor without requiring the control unit of the bioreactor to be able to control the specific components of the mixing system.

According to another aspect of the invention, the mixing system further comprises a pH sensor operatively connected to the control unit and arranged to measure a pH value in the mixing unit, and the control unit further comprises an input for receiving pH data from a bioreactor. Thereby, pH feedback from the media mixture inside the mixing unit can be used to determine the supply of further media portions, and thanks to the pH input given by the bioreactor the pH of the media mixture can be adapted to fit the specific needs of the bioreactor at any given time. Preferably, the control unit is able to receive pH data from the pH sensor and from the input, and the control unit is arranged to control operation of the first feeding mechanism in response to the pH data.

According to another aspect of the invention, the mixing system further comprises a refrigeration mechanism arranged to maintain contents of at least one of the supply units at a first predetermined temperature. Thereby, media that is best stored at a specific temperature can be maintained at optimal conditions. Preferably, the refrigeration mechanism is further arranged to maintain contents of at least one of the supply units at a second predetermined temperature that is different from the first predetermined temperature. Thereby, media that is suitable for storage at different temperatures can each be maintained at their optimal storage temperature within the same system.

According to another aspect of the invention, the mixing system further comprises a temperature sensor operatively connected to the control unit and arranged to measure a temperature in the mixing unit, wherein the control unit is also arranged to control the first feeding mechanism in response to input from the temperature sensor. Preferably, there is also provided a heating mechanism arranged to heat media in the mixing unit or in at least one of the supply units. Thereby, the temperature of the media mixture can be controlled and adapted so that the resulting media mixture for feeding into the bioreactor is at any desired value, while simultaneously allowing for refrigerated storage of the media in the supply units.

According to another aspect of the invention, the mixing system further comprises a second feeding mechanism arranged to feed media from the mixing unit to a bioreactor. Thereby, the media mixture in the mixing unit can be supplied to the bioreactor as desired.

According to another aspect of the invention, the control unit is arranged to control the mixing system in response to a predetermined program. Thereby, a sequence of media mixtures having the same or differing properties can be prepared at predetermined intervals, to allow for insertion into a bioreactor at suitable times for the cell cultivation taking place there.

According to another aspect of the invention, the control unit is arranged to control the mixing system in response to input from a user. Thereby, a dynamic control is enabled where a user can give specific input and allow for a preparation of a media mixture corresponding to that input.

Many additional benefits and advantages of the invention will become readily apparent to the person skilled in the art in view of the detailed description below.

DRAWINGS

Figure 2:
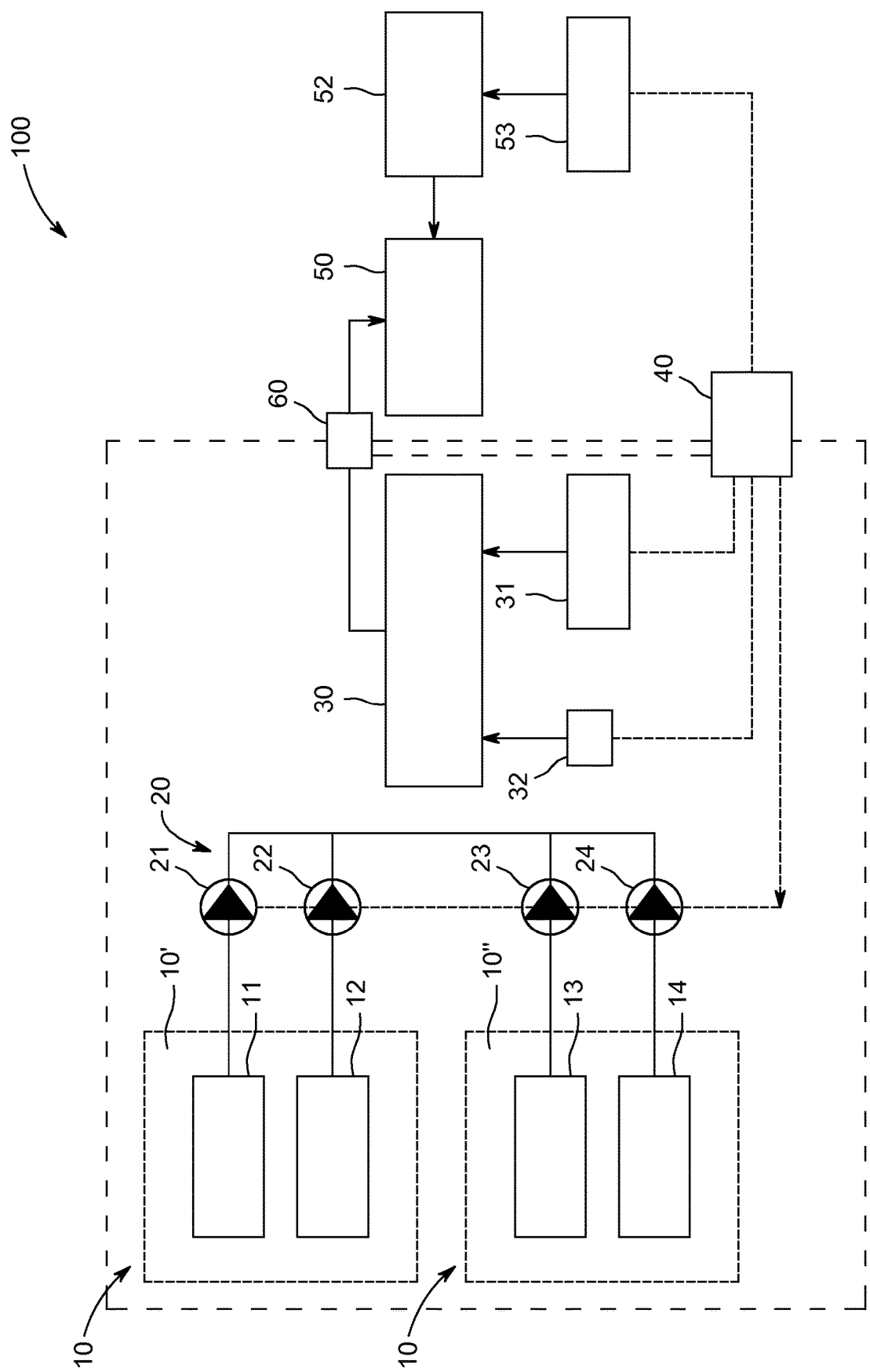
Figure 3A:
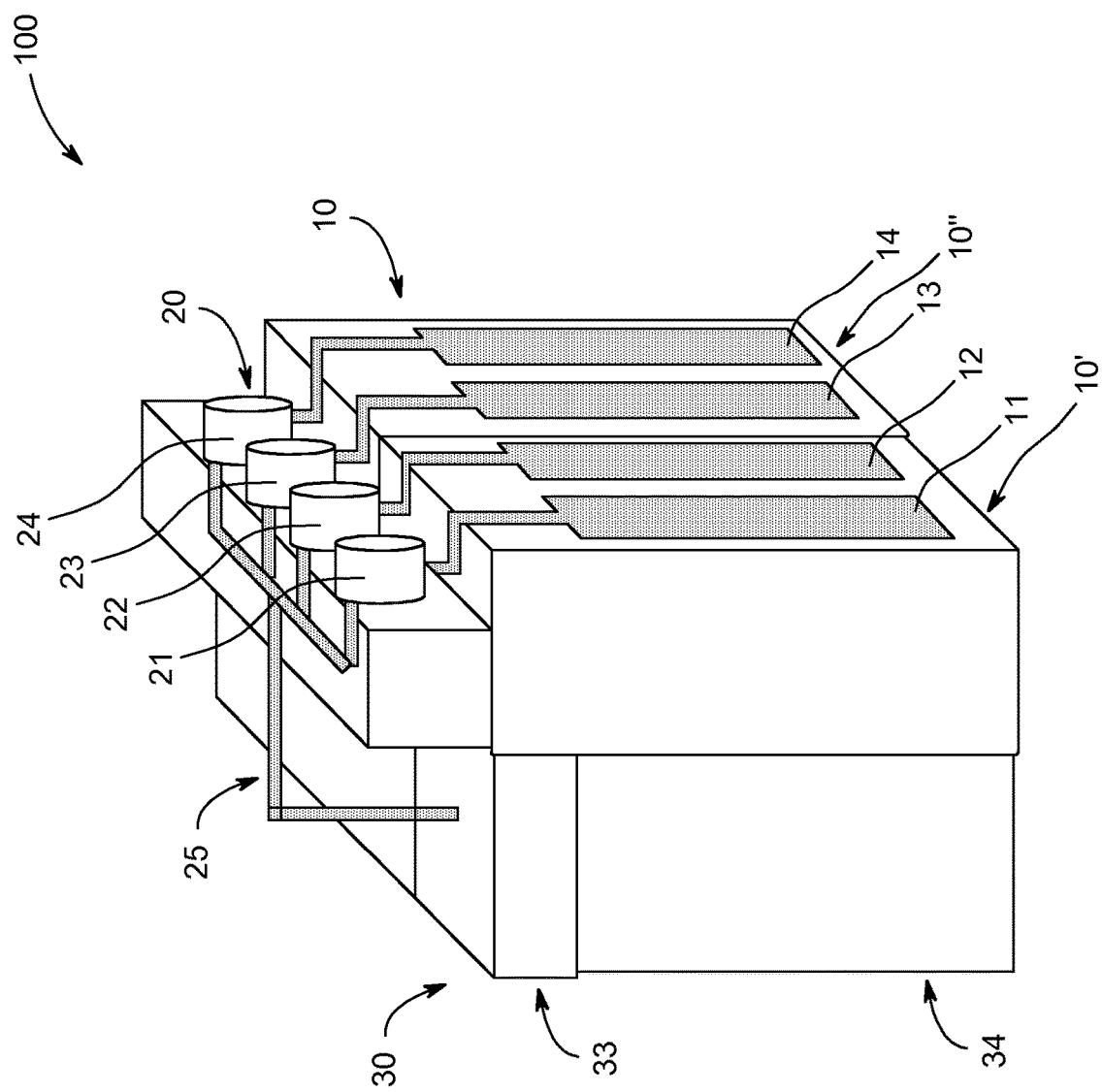
Figure 3B:
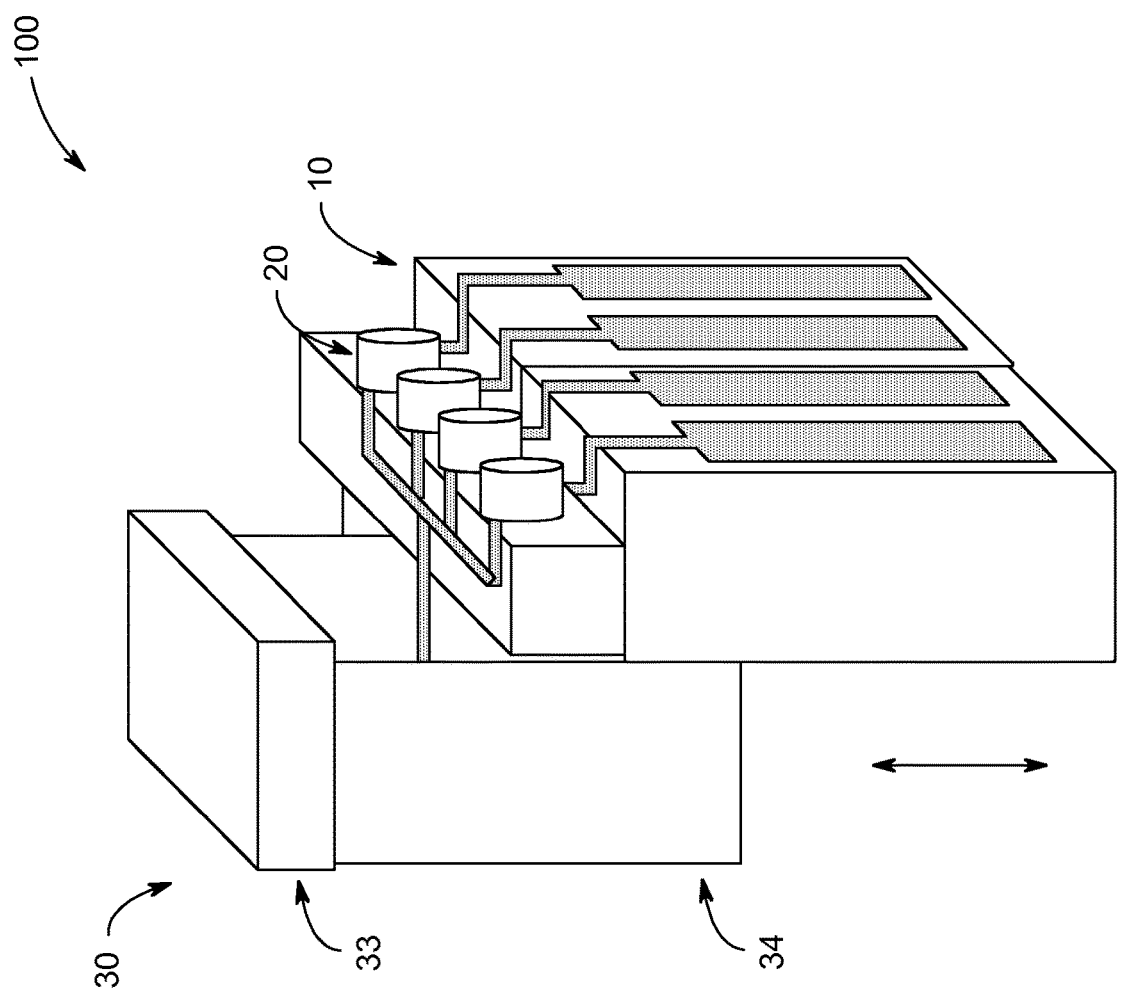
Figure 3C:
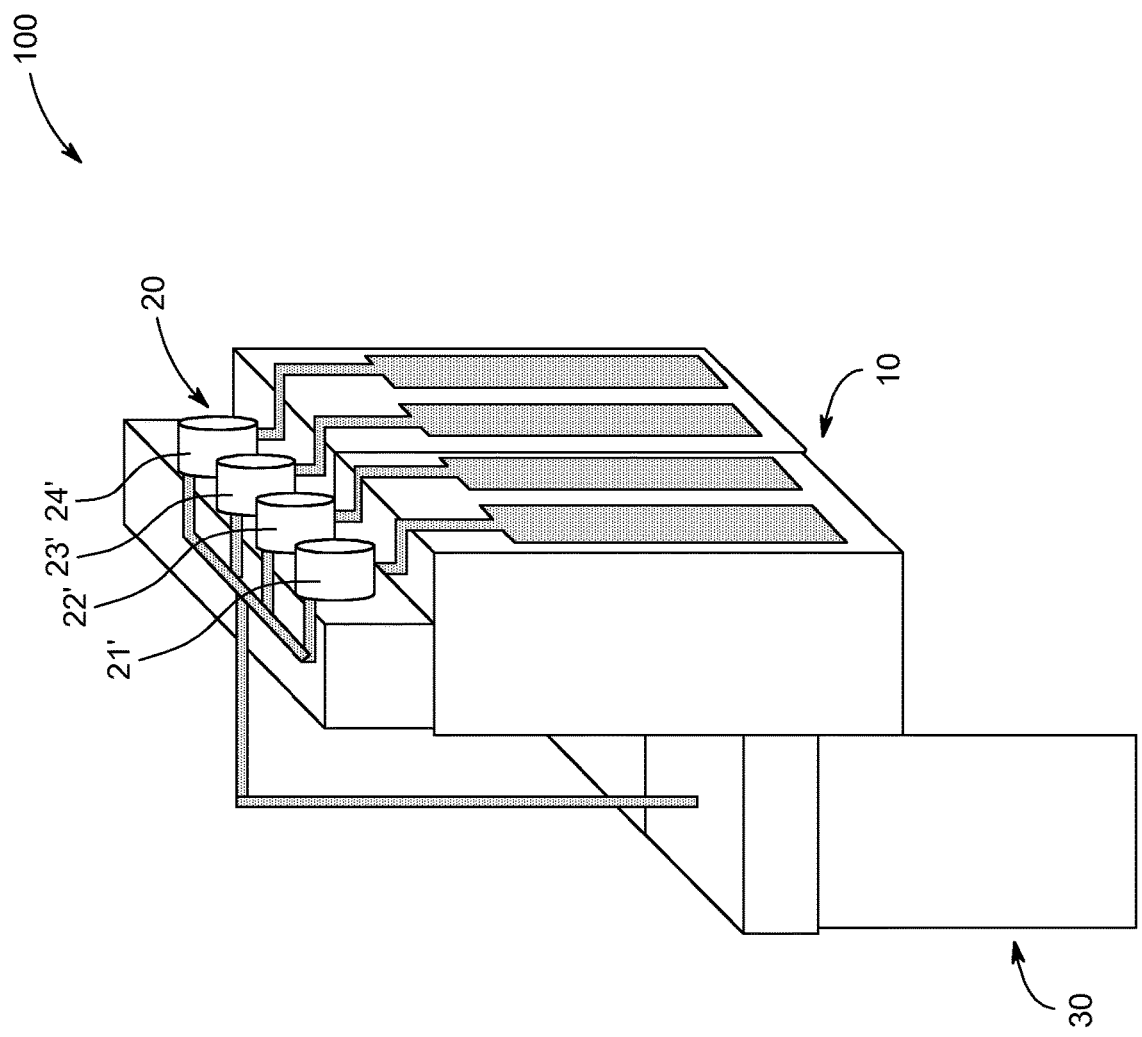
Figure 4A:
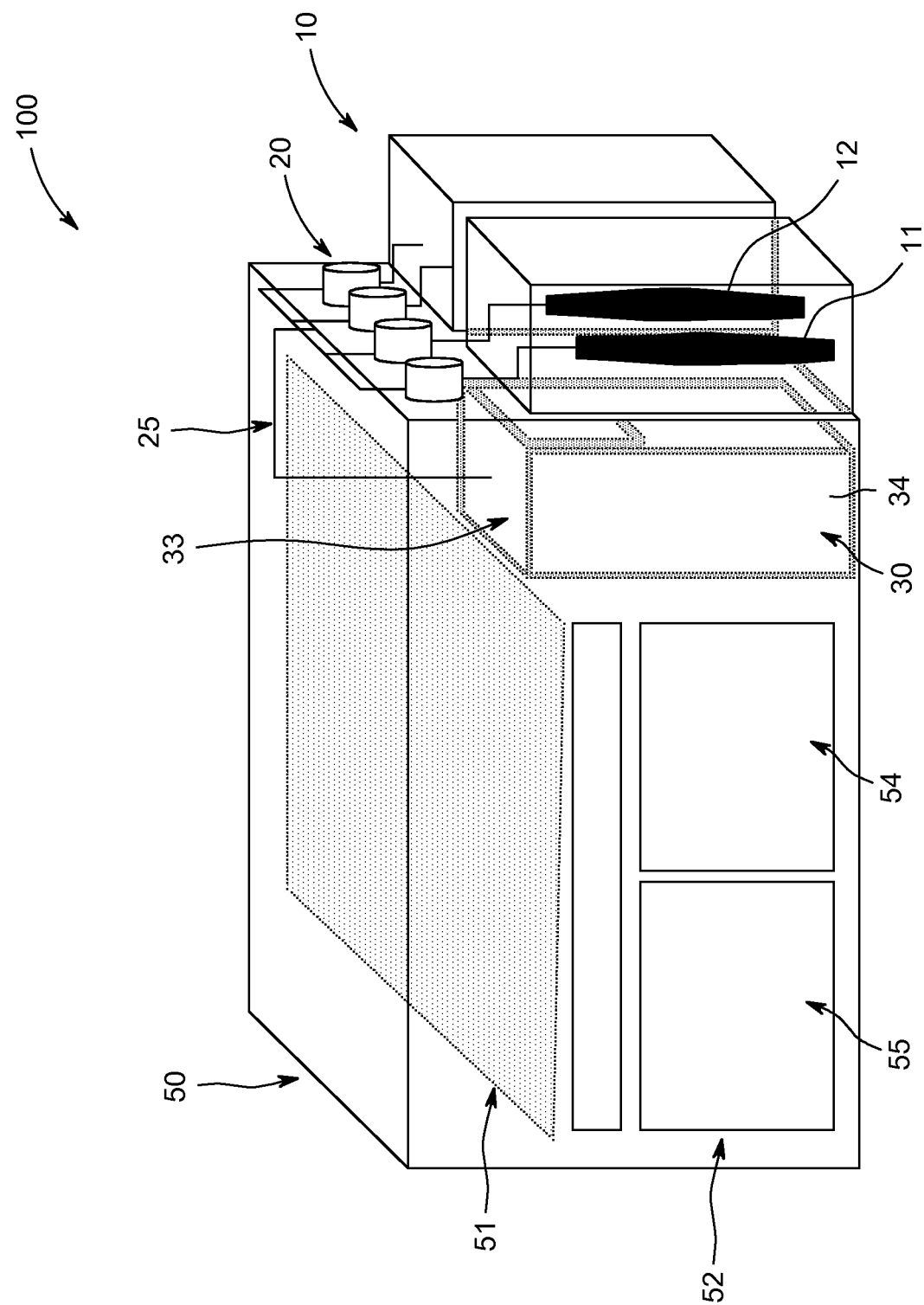
Figure 4B:
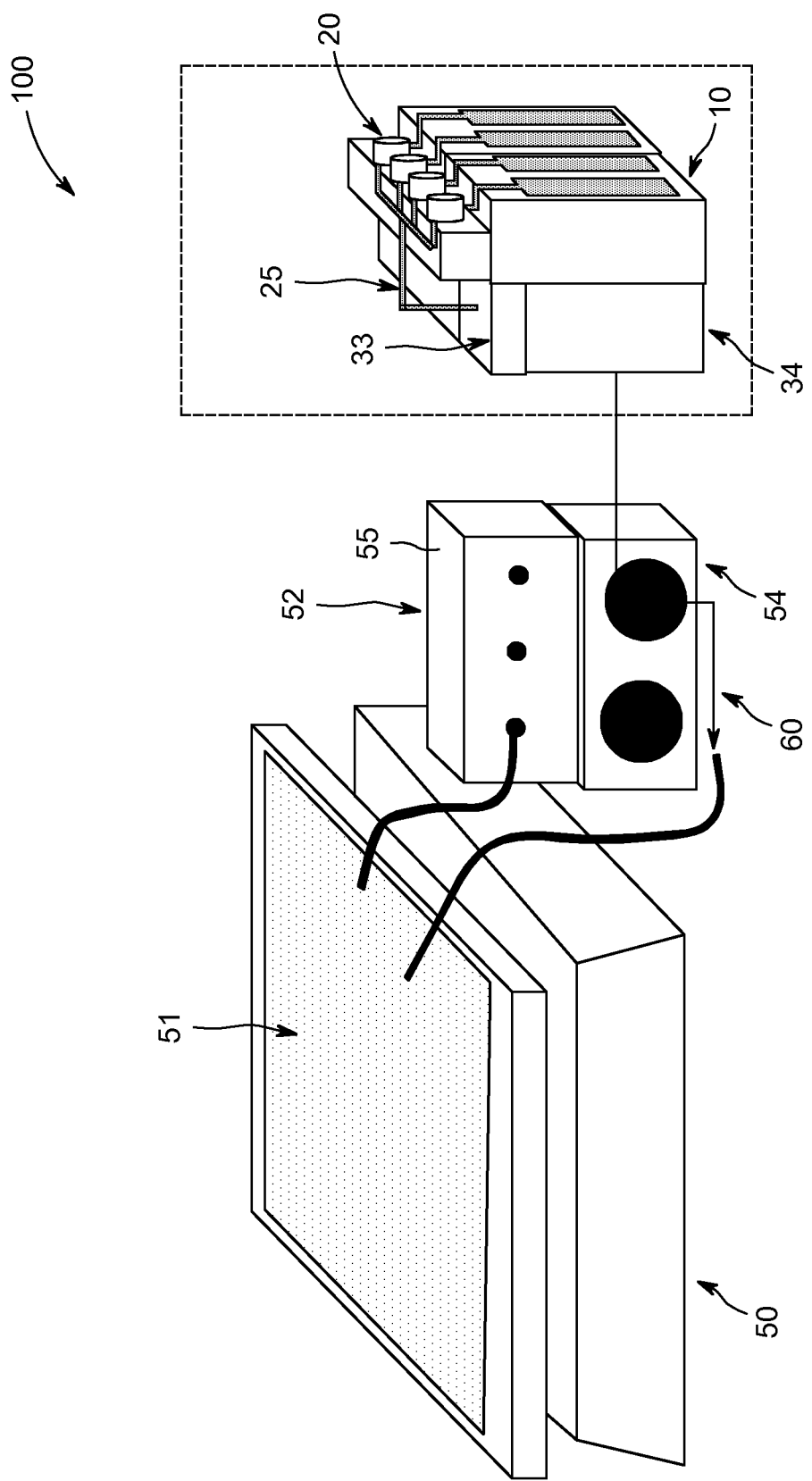
Figure 5:
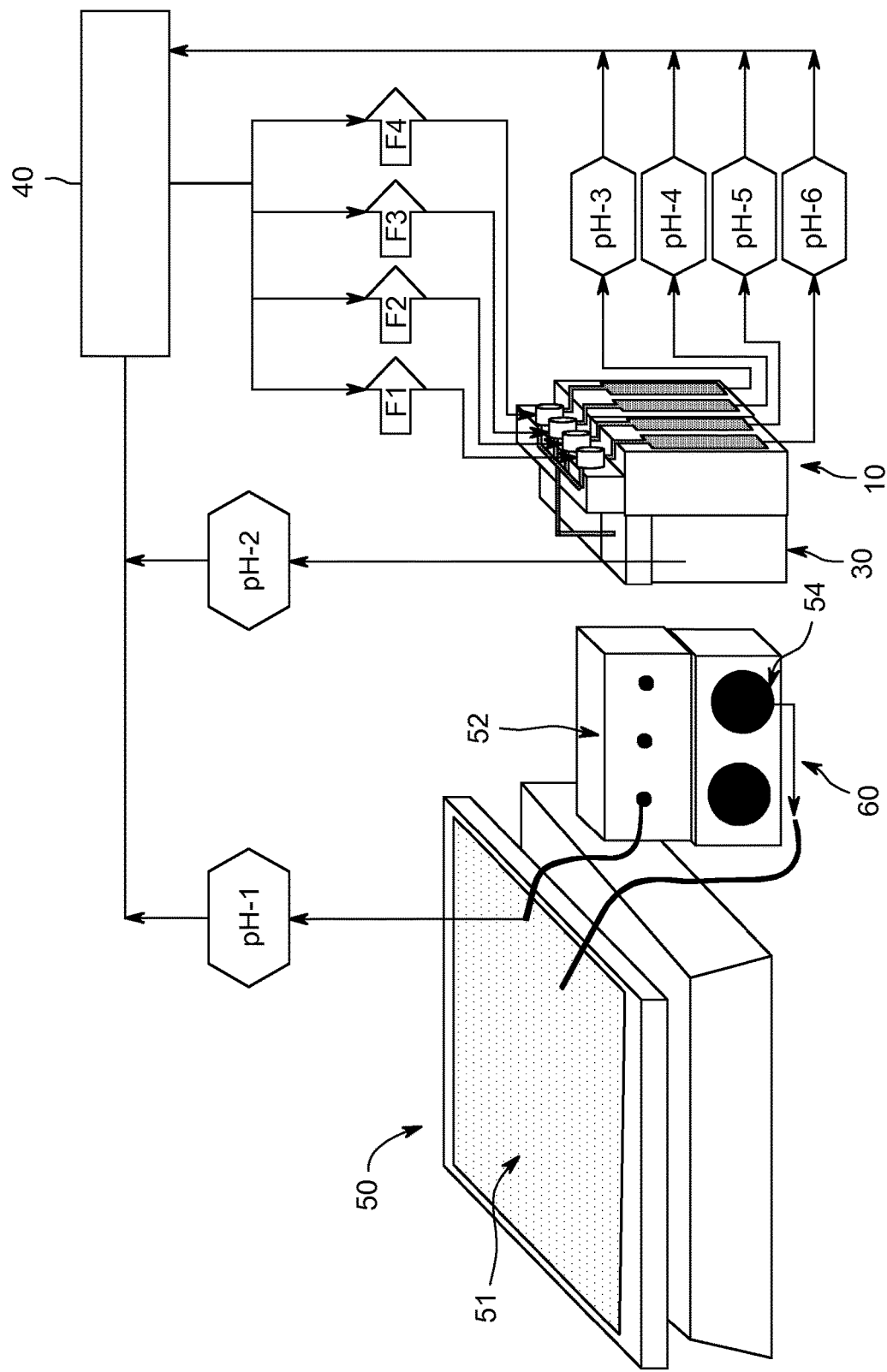

The invention will now be described in more detail with reference to the appended drawings, wherein FIG. 1 discloses a schematic view of a mixing system according to a preferred embodiment of the present invention;

FIG. 2 discloses a schematic view in more detail of the mixing system of FIG. 1;

FIG. 3a discloses a perspective view of a mixing system according to an embodiment of the present invention;

FIG. 3b discloses a perspective view of an alternative embodiment of the present invention;

FIG. 3c discloses a perspective view of another alternative embodiment of the present invention;

FIG. 4a discloses a perspective view of an embodiment of the present invention where the mixing system is integrated with a bioreactor;

FIG. 4b discloses a perspective view of an embodiment of the present invention where the mixing system is a stand-alone system; and FIG. 5 is a schematic view of an embodiment of the present invention, disclosing interaction of various parts of the mixing system with a control unit;

DETAILED DESCRIPTION

FIG. 1 discloses a mixing system 100 according to a preferred embodiment of the present invention, wherein supply units 10 are connected to a mixing unit 30 via a first feeding mechanism 20 that is able to feed media stored in the supply units 10 to the mixing unit 30. Also provided is a control unit 40 operatively connected to the mixing unit 30 and to the first feeding mechanism 20 and able to control their operation to achieve a desired feeding of media into the mixing unit 30 and a mixing to achieve a desired media mixture suitable for feeding to a bioreactor, as will be described in more detail further below. A bioreactor is a generally closed volume which is ideally sterile, for culturing cells or microorganisms, for example a flexible bag-type bioreactor often called a cell bag.

Sensors may also be provided at the mixing unit 30, such as a pH sensor 31 and a temperature sensor 32 that are arranged to measure a pH value and a temperature in the mixing unit 30 and transmit these to the control unit 40. The control unit 40 can also be provided with an input 41 for receiving input from a bioreactor as will also be described further below, and there may also be a user interface 42 connected to the control unit 40 and able to feed input from a user into the control unit 40 as well as present output from the control unit 40 to the user.

FIG. 2 discloses the mixing system 100 in more detail and also shows a bioreactor 50 able to receive media from the mixing unit 30. Thus, the supply unit 10 comprises media containers 11, 12, 13, 14 that each hold a supply of a type of media suitable for use in a bioreactor. The media containers 11, 12, 13, 14 are in this embodiment held by two supply holders 10', 10" that provide refrigeration and protection from light and other factors that may affect the media. The temperature in one of the supply holders 10' may differ from the temperature in the other supply holder 10" if that is suitable for the media types stored therein. The number of supply holders 10', 10" in the supply unit 10 may also differ depending on the media types stored in the mixing system 100. Thus, the supply holders 10', 10" also serve as refrigeration mechanisms 10', 10".

The first feeding mechanism 20 in this embodiment comprises a plurality of pumps 21, 22, 23, 24, each connected to one of the media containers 11, 12, 13, 14 by means of conduits so that media may be transported through the conduits and pumped by the pumps 21, 22, 23, 24, who are further connected via conduits to the mixing unit 30. The pumps 21, 22, 23, 24 are preferably peristaltic pumps and can be driven by stepper motors in order to pump desired amounts of media to the mixing unit 30. Depending on the mixture of media desired at a specific time, the pumps 21, 22, 23, 24 can control the flow of each type of media. This may be controlled dynamically by the control unit 40.

When the media reaches the mixing unit 30, it is mixed so that the different types of media supplied form a uniform mixture. The temperature and pH value of the mixture may also be controlled via feedback from temperature sensor 52 and/or pH sensor 53 and a heating mechanism provided in the mixing unit 30 to heat the media to the desired temperature, measured by temperature sensor 32. The heating mechanism 34 is preferably integrated with a tank 34 of the mixing unit 30. The pH sensor 31 detects a pH value of the mixture and the control unit 40 can then control the pH by operating the first feeding mechanism 20 so that media of a desired type and quantity can be fed into the mixing unit 30 and bring the media mixture to the desired pH value.

In one embodiment, the mixing unit 30 may comprise a mixer at an inlet to the mixing unit 30, said mixer being connected to a tank for holding the mixture. The sensors 31, 32 are then provided inside the tank in order to be in contact with the mixture. Also provided is an outlet connected to a second feeding mechanism 60 for feeding the mixture into a bioreactor 50.

The second feeding mechanism 60 may be controlled by the control unit 40, or may alternatively be controlled by the bioreactor 50.

FIG. 3a discloses the mixing system 100 of FIG. 1-2 in a perspective view, with the supply units 10 comprising two supply holders 10', 10" each holding two disposable bags that form the media containers 11, 12, 13, 14. Via conduits from each media container 11, 12, 13, 14 to peristaltic pumps 21, 22, 23, 24 of the first feeding mechanism 20, media is pumped from each disposable bag and led through a common conduit 25 in the form of a tube to the mixing unit 30. The mixing unit 30 comprises a mixer 33 through which the media passes to be mixed and heated before entering the tank 34, that also comprises a heater or warmer for controlling the temperature of the media mixture. The mixing system 100 is in this embodiment mounted to form a compact unit and can be connected to a bioreactor via an outlet conduit (not shown) from the tank 34. The control unit can also be mounted in the mixing system 100 directly or can be placed remotely and connected via a wire connection or wireless connection to be able to control the operation of the mixing system 100. Alternatively, the control unit can be integrated with a bioreactor or form part of a bioreactor, giving the advantage of using data from the bioreactor, such as properties of the contents of the cell bag, as input for controlling the mixing system 100.

FIG. 3b shows an alternative embodiment that differs from that shown by FIG. 3a in that the mixing unit 30 is elevated (as shown by the vertical arrows beneath the tank 34). This allows for a supply of media to the bioreactor without using a pump in the second feeding mechanism. In a similar alternative embodiment disclosed by FIG. 3c, the mixing unit 30 is lowered with regard to the supply units 10, to allow for a replacement of the pumps 21, 22, 23, 24 with valves 21', 22', 23', 24' in order to use gravitational force for transporting media from the supply units 10 to the mixing unit 30.

In an embodiment shown by FIG. 4a, the mixing system 100 is integrated with a bioreactor 50 and controlled by a bioreactor control unit 55. The components of the mixing system 100 are essentially the same as in FIG. 3a, and the tank 34 of the mixing unit 30 is connected to a cell bag 51 of the bioreactor 50 in order to supply a media mixture suitable for that cell bag 51. The CBCU is also connected to a plurality of sensors measuring properties of the cultivation process in the cell bag 51, among them a pH sensor 53 that determines the pH value inside the cell bag. Depending on the properties of the contents of the cell bag 51, the composition of the media mixture from the mixing system 100 is designed to be suitable and is prepared and mixed by the mixing system 100 for insertion into the cell bag 51 as controlled by the bioreactor control unit 55. A pump unit 54 is also provided in the bioreactor 50 for pumping nutrients into the cell bag 51 and waste products from the cell bag 51, and this pump unit 54 may also serve as the second feeding mechanism 60 for feeding the media mixture from the mixing unit 30 to the cell bag 51.

FIG. 4b discloses another embodiment, where the mixing system 100 is a standalone unit that is connectable to a bioreactor 1 via a second feeding mechanism 60 in the form of a pump unit 54. The mixing system 100 is also operatively connected to bioreactor control unit 55 that controls both the bioreactor 50 and the mixing system 100 and thus serves as the control unit 40 for the mixing system 100.

FIG. 5 discloses the standalone embodiment of FIG. 4b and shows more clearly a feedback system for controlling the pH value of the cell bag 51 by means of the control unit 40, by receiving pH measurements from the cell bag 51 itself (pH-1) and from the tank 34 (pH-2) of the mixing unit 30 as well as the pH values of the individual media in each media container 11, 12, 13, 14 (pH-3, pH-4, pH-5 and pH-6, respectively). The control unit 40 may be in the form of a microcontroller. Based on the pH values measured inside the cell bag 51, mixing unit 30 and media containers 11, 12, 13, 14, the control unit 40 determines suitable quantities of each media type from the media containers 11, 12, 13, 14 for insertion into the mixing unit 30, so that the resulting media mixture inserted into the cell bag 51 can affect the pH value of the contents of the cell bag 51 in a desired way. The control unit 40 then controls the operation of pumps 21, 22, 23, 24 (F1, F2, F3 and F4, respectively) to achieve this media mixture in the mixing unit 30.

The operation of the mixing system 100 according to the invention will now be described in more detail below.

When a supply of media is required to a bioreactor, a desired media mixture is determined, either by the bioreactor control unit 55 or by the control unit 40 of the mixing system 100 itself. In some instances, the desired media mixture can also be predetermined and given as input to the mixing system 100 by a user (dynamic input) or by a separate unit or protocol.

The control unit 40 then determines suitable media portions of different types for forming said desired media mixture and allows these media portions to be conducted from the supply units 10 to the mixing unit 30 by operating the first feeding mechanism 20 to transport media from each media container 11, 12, 13, 14 of the supply units 10 according to the media portions selected of each type. In the mixing unit 30, the media is thoroughly mixed by means of a mixer and is also generally heated to a desired temperature. The media mixture is then ready to be fed to the bioreactor 50 and inserted into the cell bag 51.

Thanks to the sensors for measuring pH and temperature 31, 32, and to possible other sensors arranged in connection with the mixing unit 30, the conditions of the media mixture can be continuously monitored by the control unit. Thus, if the media mixture does not have the desired properties, for instance with regard to the pH value, the control unit 40 can control the first feeding mechanism 20 to supply an additional portion of any of the available media types in the media containers 11, 12, 13, 14 and thereby alter the pH value of the resulting media mixture. Through the temperature monitoring, the heater provided in the mixing unit 30 can also be controlled to alter the temperature of the media mixture as desired.

In some embodiments, the control unit 40 is provided with input through a user interface 42 and performs the mixing of media portions according to predetermined parameters, possibly using pH feedback from the pH sensor 31 and temperature feedback from temperature sensor 32 to ascertain that the resulting media mixture has the desired properties given by the input from the user interface 42. The operation of the mixing system 100 is in such an embodiment independent from the bioreactor 50.

In other embodiments, however, the operation of the mixing system 100 can be controlled by the bioreactor 50 itself, through input to the input 41 of the control unit. In one embodiment, the mixing system 100 is slave to the bioreactor, and in another embodiment the mixing system 100 may be integrated with the bioreactor control unit 55 of the bioreactor 50 itself.

In some embodiments, the mixing system 100 may also act independently of the bioreactor but receive input through input 41, for instance giving parameters such as temperature, pH value and quantity of media present in the cell bag 51. These parameters are used for deciding the desired media mixture, and allows the control unit 40 to determine the media portions of each media type that are to be inserted into the mixing unit 30. In such embodiments, feedback from the mixing unit 30 such as pH and temperature feedback, may also be used to further improve the media mixture.

It is especially beneficial that the mixing system 100 may act independently from a user or operator, providing a desired media mixture at predetermined times and in response to the needs of the bioreactor 50. The system is also a closed system, preventing contamination of the media and providing high quality media for the bioreactor.

In some embodiments, the mixing system 100 may act according to a predetermined program where a media mixture having specific properties is prepared at given time intervals. This can also be combined with the opportunity for a user to interrupt or modify the program dynamically by giving additional input through the user interface 42 so that the prepared media mixture corresponds to a combination of the predetermined program and more recent input.

In some embodiments, the monitoring and controlling of pH of the media mixture comprises detecting a current pH value of the media mixture in the mixing unit, determining a pH correction to arrive at a desired pH value of the media mixture, and identifying a media portion corresponding to said pH correction and supplying that media portion to the media mixture in the mixing unit. Thus, by selecting a suitable media portion having a pH value that will affect the pH of the media mixture as a whole, its pH can be controlled and adjusted. The desired pH value can be determined based on pre-programmed information in the control unit 40 or on dynamic input by a user, but it can also be based on input received from the bioreactor 50. Preferably, the temperature of the media mixture is monitored as described above and the media mixture is heated to arrive at a desired temperature.

The method according to the present invention may be performed as a computer-implemented method and be stored on a computer-readable storage medium as is well known within the art. The control unit 40 and other components of the invention can form a data processing system comprising means for carrying out the method. Software comprising instructions for carrying out the method steps may also be stored as a computer program product, as is also well-known within the art.

It is to be noted that features of the various embodiments of the invention described herein may freely be combined, unless it is explicitly stated that such a combination is unsuitable.

The invention claimed is:

1. A mixing system for a bioreactor, for producing a mixture prior to it being fed into the bioreactor, the mixing system comprising: a cell bag; a plurality of supply units, each being able to hold media for use in a bioreactor; a mixing unit for creating a uniform mixing of media; a first feeding mechanism, arranged to feed media from the supply units into the mixing unit; a second feeding mechanism arranged to feed media from the mixing unit to the cell bag; a refrigeration system configured to maintain contents of a first supply unit of the plurality of supply units at a first temperature, and of a second supply unit of the plurality of supply units at a second temperature; and a control unit operatively connected to the first feeding mechanism and the mixing unit, said control unit being configured to control the first feeding mechanism to feed predetermined amounts of media from the plurality of supply units to the mixing unit, further being configured to control the mixing unit to create a uniform mixing of media, and further being configured to control the mixing system to control a temperature of the mixture.

2. The mixing system according to claim 1, wherein the mixing system is integrated with a bioreactor.

3. The mixing system according to claim 1, wherein the first feeding mechanism comprises pumps for pumping media from each of the supply units to the mixing unit and wherein the pumps are peristaltic pumps.

4. The mixing system according to claim 1, wherein the first feeding mechanism comprises valves for controlling a flow of media from each of the supply units to the mixing unit.

5. The mixing system according to claim 1, wherein the bioreactor is operatively connected to and able to control the operation of the mixing unit.

6. The mixing system according to claim 3, wherein the peristaltic pumps are controlled by at least one stepper motor.

7. The mixing system according to claim 1, further comprising a pH sensor operatively connected to the control unit and arranged to measure a pH value in the mixing unit, and wherein the control unit further comprises an input for receiving pH data from a bioreactor.

8. The mixing system according to claim 7, wherein the control unit is able to receive pH data from the pH sensor and from the input, and wherein the control unit is arranged to control the operation of the first feeding mechanism in response to the pH data.

9. The mixing system of claim 8, wherein the control unit is further configured to control the mixing system to control a pH of the mixture.

10. The mixing system according to claim 1, wherein the refrigeration system is further arranged to maintain contents of at least another of the supply units at another predetermined temperature that is different from the first or second predetermined temperatures.

11. The mixing system according to claim 1, further comprising a temperature sensor operatively connected to the control unit and arranged to measure a temperature in the mixing unit, wherein the control unit is also arranged to control the first feeding mechanism in response to input from the temperature sensor.

12. The mixing system according to claim 1, further comprising a heating mechanism arranged to heat media in the mixing unit or in at least one of the supply units.

13. The mixing system according to claim 1, wherein the control unit is arranged to control the mixing system in response to a predetermined program.

14. The mixing system according to claim 1, wherein the control unit is arranged to control the mixing system in response to input from a user.

* * * * *